(12) United States Patent
Duckett

(10) Patent No.: US 6,498,642 B1
(45) Date of Patent: Dec. 24, 2002

(54) ENDOSCOPE INSPECTION SYSTEM

(75) Inventor: George E. Duckett, Charlton, MA (US)

(73) Assignee: Karl Storz Endovision, Charlton, MA (US)

( * ) Notice: Subject to any disclaimer, the term of this patent is extended or adjusted under 35 U.S.C. 154(b) by 0 days.

(21) Appl. No.: 09/563,866

(22) Filed: May 3, 2000

(51) Int. Cl.[7] ............................ G01N 21/01; G01J 1/00; G01B 9/00
(52) U.S. Cl. ................ 356/244; 356/213; 356/73.1; 356/124; 356/124.5; 356/237.2; 600/103; 600/108; 600/127
(58) Field of Search ..................... 356/213, 73.1, 356/121, 124, 124.5, 125, 127, 244, 247, 388, 237.2; 600/103, 108, 117, 127

(56) References Cited

U.S. PATENT DOCUMENTS 4,418,689 A  * 12/1983  Kanazawa ................ 600/108
5,694,214 A  * 12/1997  Watanabe et al. ........ 356/237.2
6,069,691 A  *  5/2000  Rosow et al. ............ 356/124.5
6,388,742 B1 *  5/2002  Duckett .................... 356/73.1

* cited by examiner

Primary Examiner—Loha Ben
(74) Attorney, Agent, or Firm—St. Onge Steward Johnston & Reens LLC

(57) ABSTRACT

An inspection system for performing a test selected from the group consisting of field of view, angle of view, distortion, image quality, depth of field, illumination system transmission efficiency, illumination profile, relative transmission of imaging system and centering error of a rigid, rod lens endoscope. The inspection system includes a testing station supporting a plurality of targets for measuring an optical performance of the endoscope, and a controller controllably displacing the testing station linearly toward and away from the endoscope and rotating the testing station at a nominal angle of view of the endoscope about a first axis and rotating the targets about a second axis parallel to the first axis to selectively displace each of the targets into the field of view of the endoscope.

20 Claims, 8 Drawing Sheets

FIG. 11

TEST PARAMETERS — 118

| | |
|---|---|
| ENTRANCE PUPIL LOCATION | 1.080000 |
| COUPLER TO USE | 25 mm |
| ANGLE OF VIEW (NOM.) | 60.0 |
| NOMINAL OBJECT DISTANCE | 35 |
| OTHER DEPTH OF FIELD DISTANCES #1 | 55 |
| OTHER DEPTH OF FIELD DISTANCES #2 | 25 |
| OTHER DEPTH OF FIELD DISTANCES #3 | 15 |
| OTHER DEPTH OF FIELD DISTANCES #4 | 10 |
| OTHER DEPTH OF FIELD DISTANCES #5 | 8 |
| OTHER DEPTH OF FIELD DISTANCES #6 | 5 |

SCOPE PARAMETERS — 124

| | |
|---|---|
| ANGLE OF VIEW | 60.0 |
| FIELD OF VIEW | 80.71 |
| DISTORTION 1.0 FIELD | -23.74 |
| DISTORTION 0.7 FIELD | -13.93 |
| ILLUMINATION EFFICIENCY | 0.209 |
| AVERAGE PEAK/EDGE ILL. | 0.487 |
| IMAGE QUALITY (BEST FOCUS) | |
| IMAGE QUALITY (INFINITY FOCUS) | |
| IMAGING SYSTEM | |

ADD NEW SCOPE — 122

SERIAL NUMBER — 120

SELECT SCOPE TYPE: 27005CA

LENGTH (cm): 30    DIAMETER (mm): 4

KARL STORZ RIGID ENDOSCOPE INSPECTION SYSTEM VERSION 1.0         12/20/99 : 10 : 59 AM

COMMENTS

DEPTH OF FIELD: 6.4 mm TO > 55.0 mm

| | 5 | 8 | 10 | 15 | 25 | 35 | 55 |
|---|---|---|---|---|---|---|---|
| TEST SCOPE | ○ | ○ | ○ | ○ | ○ | ○ | ○ |
| SIM. STD. SCOPE | | ○ | | | | | |

OBJECT DISTANCE (MM)

| | MEAS. | NOM. | CHANGE | P/F |
|---|---|---|---|---|
| ANGLE OF VIEW | 56.2° | 60.00° | 3.80° | PASS |
| FIELD OF VIEW | 95.2° | 80.71° | 14.49° | FAIL |
| DISTORTION 1.0 FIELD | -34.3% | -23.74% | -10.56% | |
| DISTORTION 0.7 FIELD | -22.9% | -13.93% | -8.97% | |
| ILLUMINATION SYSTEM EFFICIENCY | 0.11 | 0.21 | -0.10 | |
| RELATIVE BRIGHTNESS-IMAGING SYSTEM | 0.51 | 1.00 | -0.49 | |
| EDGE/PEAK ILLUMINATION AVERAGE | 0.31 | 0.49 | -0.18 | |
| CENTERING ARROR | 4.60% | 0.00% | 4.60% | |

IMAGE ANALYSIS
STD SCOPE IMAGE

IMAGE ANALYSIS
(CAMERA FOCUS INF)
STD SCOPE INF IQ

ILLUM. ANALYSIS
STD SCOPE ILLUM.

FIG. 12

ENDOSCOPE INSPECTION SYSTEM

SUMMARY OF THE INVENTION

The present invention relates to a method and apparatus for testing optical systems. More particularly, this invention relates to a method and apparatus for checking and measuring optical data of optical assemblies for endoscopes. Specifically, this invention relates to a method and apparatus for testing endoscopes of different physical and optical configurations.

BACKGROUND OF THE INVENTION

Endoscopic image transmitting optical systems are extensively used to permit visualization of typically inaccessible areas within a patient's body. These systems generally include a housing enclosing a lens portion for focusing and relaying an image, and an illumination means for illuminating the region to be viewed. In endoscopic surgical procedures, relatively narrow surgical instruments are inserted into the patient's body so that the distal (i.e., working) ends of the instruments are positioned at a remote interior site, while the proximal (i.e., handle) ends of the instruments remain outside the patient's body. The surgeon then manipulates the proximal handle ends of the instruments as required so as to cause the distal working ends of the instruments to carry out the desired surgical procedure at the remote interior site.

The endoscope generally comprises an elongated shaft having a distal end and a proximal end, and at least one internal passageway extending between the distal end and the proximal end. An image capturing device is disposed at the distal end of the shaft and extends through the shaft's internal passageway to capture an image of a selected region located substantially adjacent to the distal end of the shaft and convey that image to the proximal end of the shaft. A viewing device is in turn disposed adjacent to the proximal end of the shaft, whereby the image obtained by the image capturing device can be conveyed to a display device which is viewed by the surgeon.

With this arrangement, the viewing device can comprise a display device in the form of a conventional optical viewer or eyepiece which is viewed directly by the surgeon. Alternatively, the viewing device can comprise an appropriate image sensor, e.g. a charge coupled device ("CCD") element, which receives the captured image from the proximal end of the fiber optic bundle and generate corresponding video signals which are representative of the captured image. These video signals are then displayed on an appropriate display device (e.g. a monitor) which is viewed by the surgeon.

Quality of an image transmitted by a typical endoscope critically depends on its optical performance and needs to be tested before the endoscope is used in a surgical procedure. Both a lens system and a fiber optic illumination system of an endoscopic assembly should be carefully evaluated. Thus, for instance, damaged fiber wires can be responsible for only partially transmitted light. A damaged lens system leads to a distorted image or to blurring the sharpness of image colors. To avoid these and other drawbacks in the optical performance of endoscopes as a result of the manufacturing process it is known to use diagnostic systems.

U.S. Pat. No. 4,613,232 to Diener et al. discloses a measuring device for testing optical systems of an endoscope which includes a linearly displaceable guide rail receiving a shaft of an endoscope. To evaluate different optical and physical characteristics of a tested endoscope, this reference discloses different targets, each for performing a respective test and mounted on a separate displaceable arm.

Having differently dimensioned arms may lead to complicated kinematics of the testing system because each given test has be conducted in a precise position of the respective arm with respect to the tested endoscope. To computerize such complicated system may be very difficult since every arm would need its separate access motion.

U.S. Pat. No. 5,841,525 to Rosow discloses a testing system including a linearly displaceable carrier which supports a set of different targets, each selectively aligned with a tip of an endoscope for conducting a given test. An endoscope is mounted on an angularly displaceable arm.

In order to perform different tests, the carrier must be removed, rotated at a 180° angle and repositioned in a respective alignment position, which makes computerization of this system difficult to achieve. Further, an endoscope is mounted on an upright rotatable arm whose displacement requires a lot of space that may be rather scarce at a location where an endoscope is being tested. Still another disadvantage of the system disclosed in this reference is that a single fiber optic cable is used to perform a transmission measurement of the illumination fibers. Thus, first a user measures the output of a light guide, then reattaches it to an endoscope to measure its output. The ratio of the outputs is the transmission of the endoscope. This, however, involves the user taking a measurement before and after the light guide is attached to the endoscope making the test unnecessarily complicated.

What is desired, therefore, is a testing system having a single support mechanism that can automatically perform all necessary displacements of targets adapted to conduct a variety of tests without a need to manually replace and reposition different parts. Further, a testing system for automatically evaluating and displaying the results of a variety of tests based on comparison of the performance of an endoscope to be tested with the performance of a standard endoscope is also desirable, as is a testing system for automatically conducting a series of tests on an endoscope in response to a variety of parameters introduced by a user.

SUMMARY OF THE INVENTION

A device and method for testing a variety of endoscopes in accordance with this invention address many of the above-discussed problems of the known prior art.

Particularly, a device for evaluating optical performance of endoscopes provides a variety of tests by provision of a testing station which is rotatably and linearly displaceable relative to a fixed position of a distal end of a tested endoscope.

The testing station includes a turntable rotatable about a first axis and supporting a linearly movable carousel support which, in turn, rotatably supports a carousel of targets to measure the optical performance of an endoscope.

The tests to be performed on both a flexible endoscope and a rigid, rod lens endoscope may include evaluation of field of view, angle of view, distortion, depth of field, of illumination system transmission efficiency, illumination profile, and relative transmission of imaging system and of centering error. The only difference between the flexible and rigid types is that an image quality test can be performed only on the rigid scope. It is possible to use four targets including a grid of pinholes, a diffuse but translucent white target, a single pinhole target and a luminous flux detector that should be sufficient to make all of the required measurements.

The device according to the invention is capable of testing a Karl Storz endoscope by comparing its performance with a standard scope of the same type stored in the database. Further, the device is capable of examination of any endoscope by comparing its performance with a standard Karl Storz endoscope whose characteristics stored in a database and are comparable with the characteristics of the endoscope to be tested. Alternatively, the device can test an endoscope without comparing it to a standard one and, afterwards, add a set of parameters of this new type of the endoscope to the system's database.

According to another aspect of the invention, the system has a support station adapted to receive a CCD camera which, in turn, receives an eyepiece of an endoscope to provide vertical and angular adjustment of the latter with respect to an alignment target. The support station is controllably displaceable along a horizontal rail to displace a distal end of the endoscope toward and away from the testing station.

In accordance with another aspect of the invention, the horizontal rail is mounted on a riser block which can be controllably actuated to move the support station at a predetermined vertical distance. Mounted on an opposite end of the rail is a "V" block assembly adapted to provide a correct horizontal position of the endoscope. The V block assembly has an adjustable arm formed with a V shape groove which receives a shaft of the endoscope as the block slides along the rail.

The support station in combination with the "V" block assembly allows the endoscope to be properly aligned with respect to an alignment target specifically designed to position the endoscope in a predetermined aligned position with respect to the testing station. As is known, proper alignment of an endoscope is critical. Misalignment of the endoscope can lead directly to inaccurate test data. Upon establishing the proper horizontal position, the support station is controllably displaceable to enable vertical and horizontal edges of a slit formed in the alignment target to be centered in the field of view of the tested endoscope.

An automatic process is completed by controllably rotating the carousel at predetermined angles so that each of the targets is aligned with the distal end of the scope. In accordance with the invention, each of the tests is processed and the results are displayed on a monitor.

It is therefore an object of this invention to provide a device for automatically evaluating the optical performance of an endoscope.

It is another object of the invention to provide a device for automatically evaluating the optical performance of endoscopes having varying physical characteristics.

It is still another object of the invention to provide a device for automatically evaluating the optical performance of an endoscope which has a variety of targets controllably rotatable relative to the tested endoscope to predetermined angular positions.

Still another object of the invention is to provide a device for automatically evaluating the optical performance of an endoscope which has a turntable for automatically adjusting a nominal angle of view of a tested endoscope.

It is a further object of this invention to provide a device for automatically evaluating an optical performance of an endoscope which has a linearly displaceable carousel support to provide a safe alignment of an endoscope and a predetermined distance between each of the targets and the endoscope.

Still a further object of the invention is to provide a device and method for operating this device allowing a user to perform a series of selected tests evaluating an optical performance of an endoscope.

BRIEF DESCRIPTION OF THE DRAWINGS

FIG. 11 is an exemplary display of graphical user interface provided by a computer of the device of FIGS. 1 and 2 and illustrating a selection of tests.

FIG. 12 is a display of comparative results of the scope to be tested and the standard one, and photographs of images as grabbed by a camera during conducting of a plurality of tests.

DETAILED DESCRIPTION OF THE DRAWINGS

Figure 1:
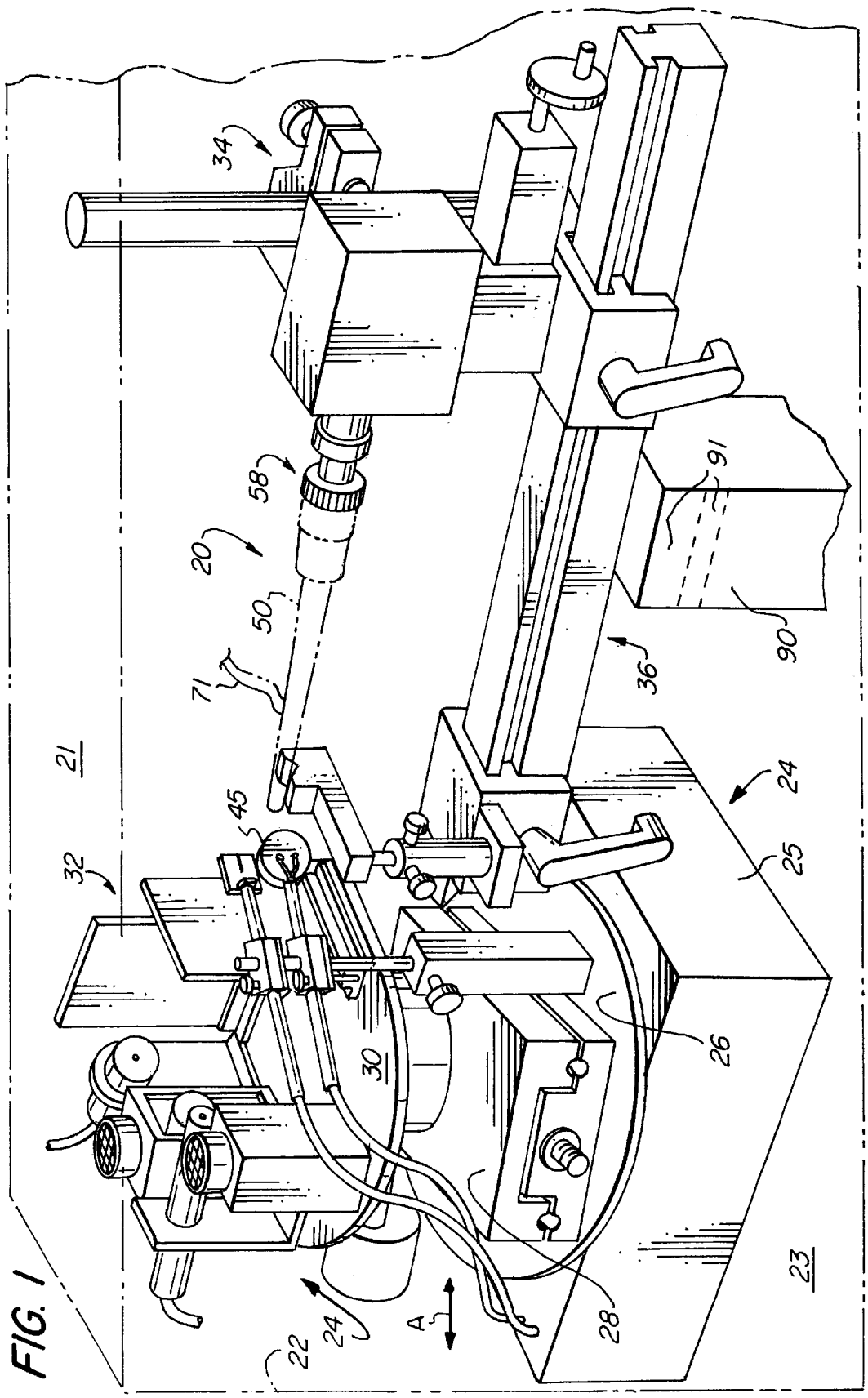
FIG. 1 is an isometric view of a device for evaluating an optical performance of an endoscope.

Referring to FIGS. 1–10, a endoscope inspection system 20 for evaluating the optical performance of an endoscope is shown. Particularly, as illustrated in FIG. 1, the inspection system 20 includes a casing 22 having a bottom 23 and provided with a closure 21 which can close the casing during inspection of an endoscope.

The casing 22 houses a testing station 24 adapted to provide a plurality of optical tests on an endoscope 50, an endoscope support station 34 and an alignment station 36 extending between the endoscope support and testing stations.

In accordance with one aspect of the invention, the testing station can be displaceable to provide a plurality of tests on an endoscope to be tested by first rotating about a first axis to a nominal angle of the endoscope. Having established a position corresponding to the nominal angle, the testing station is linearly displaceable at a nominal distance between itself and a distal end 52 of the endoscope. Finally, the testing station is rotatable about a second axis to selectively position each of an array of targets 32 in a predetermined position relative to the distal end of the endoscope.

Figure 2:
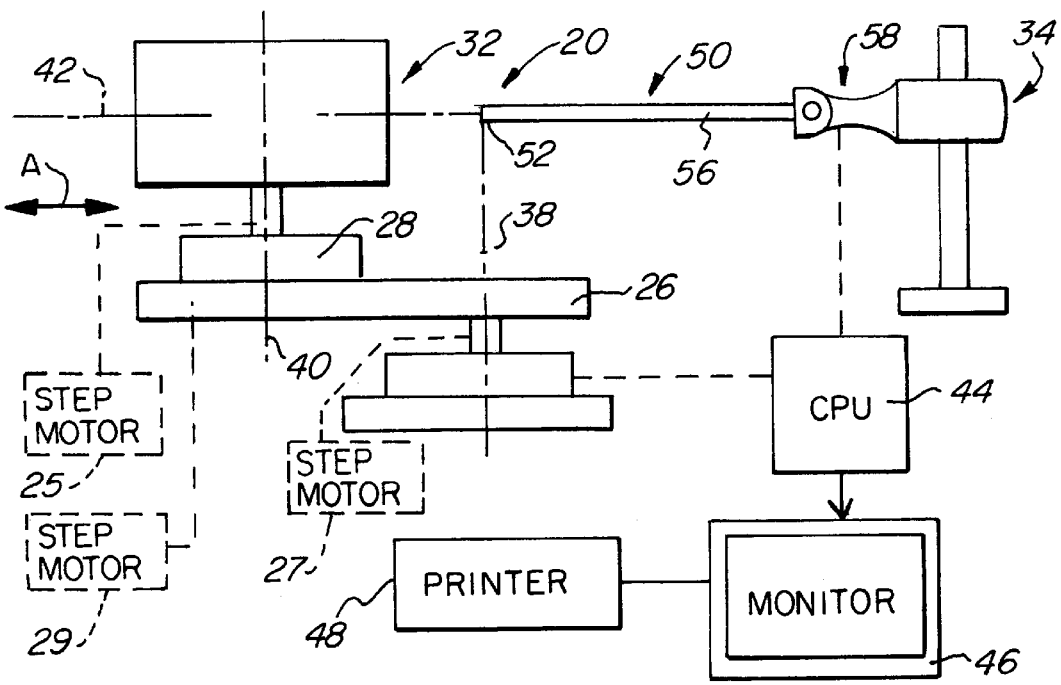
FIG. 2 is a schematic view of the device shown in FIG. 1 along with electronic equipment.
Figure 3:
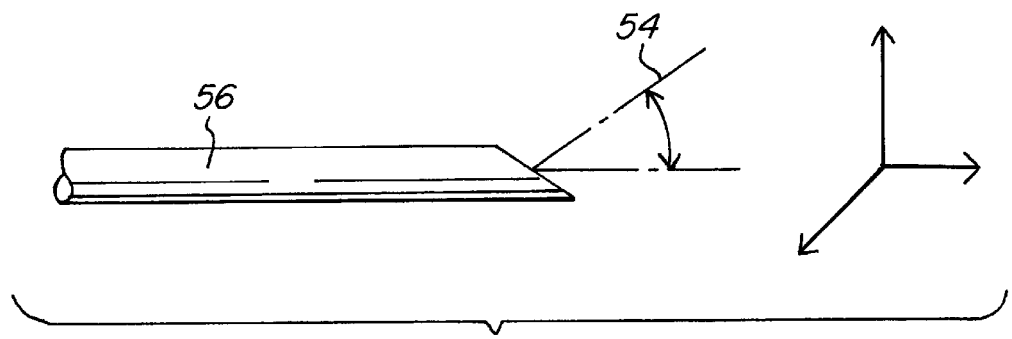
FIG. 3 is a schematic view illustrating an angle of view of an endoscope to be tested by the device shown in FIGS. 1 and 2.

Particularly, the testing station 24 includes a base 25 stationary mounted on the bottom of the casing and receiving a turntable 26. The turntable 26 is controllably rotatable about a first axis 38 by a motor 27 (FIG. 2). This rotation brings the testing station 24 to the nominal angle of view of the endoscope 50. The angle of view is defined as an angle an optical axis 54 at the distal end 52 of the endoscope makes with its shaft 56, as illustrated in FIG. 3. Depending on an operational mode of the inspection system 20, this angle can be retrieved from a database or introduced by a user, as will be explained hereinafter. Once the nominal angle of view is established, the turntable 26 will remain immovable during the entire duration of a testing procedure.

Having completed angular displacement of the turntable bringing the testing station to the nominal angle of view of the endoscope, the testing station is linearly displaceable at a nominal object distance. This is the distance at which the endoscope is to be focused and most of the tests are to be conducted. In order to establish the nominal distance, a movable carousel support 28, which is mounted on the rotary table 26, is linearly displaceable either in accordance with a value stored in the database or based on an experience and observation of a user, as will be explained hereinbelow. If a selected mode of operation necessitates testing an endoscope without comparison with the stored data, a few factors may govern the selection of nominal object distance. If the object distance is too short, few pinholes of the pinhole grid target will be available for the distortion, filed of view, and image quality tests, and the accuracy will suffer as a result. If the distance is too great, then there may be too many pixels and the testing will take an excessive amount of time and the pixels at the edge of the field of view will not be imaged properly leading to erroneous measurements.

Figure 4:
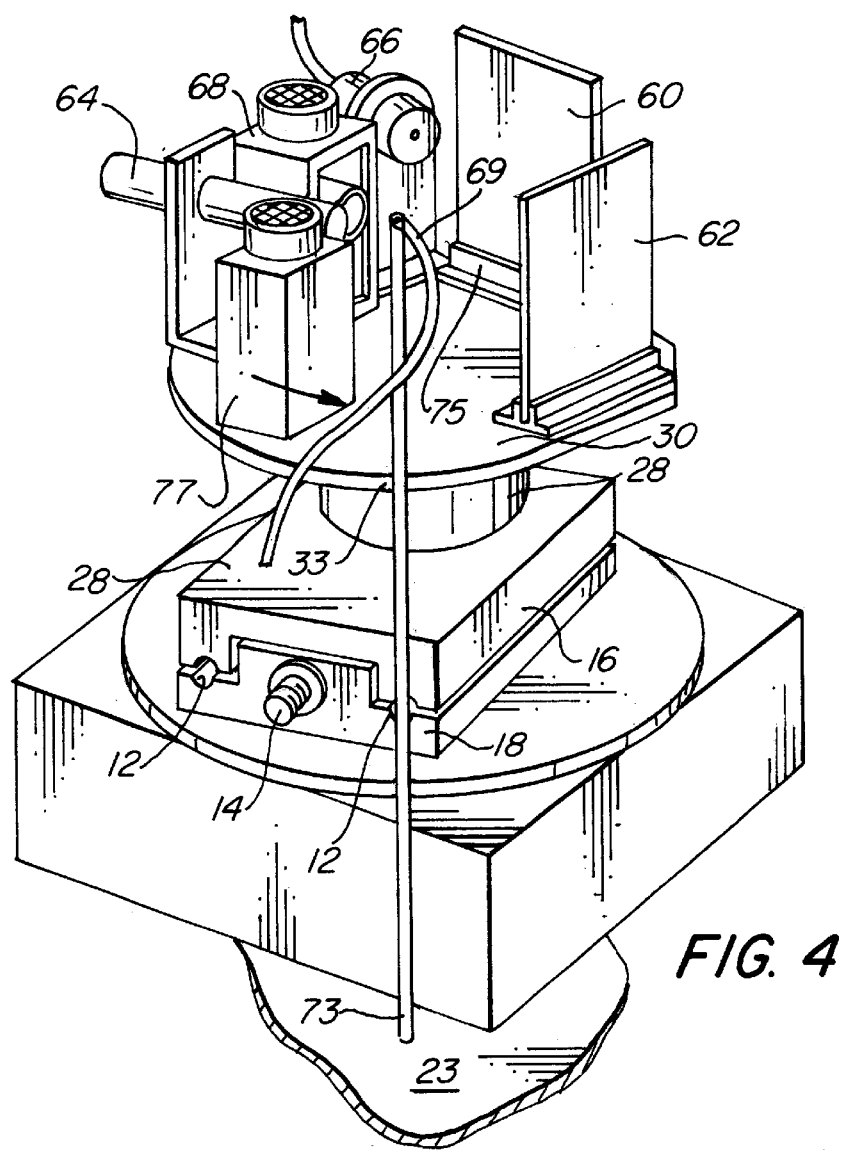
FIG. 4 is an isometric view of a carousel with a variety of targets in accordance with a device shown in FIGS. 1 and 2.

To establish a nominal distance, the movable carousel support 28, as shown in FIGS. 1 and 4 may have a fixed base 18 stationary mounted on the rotary table 26 and a movable top 16 linearly displaceable relative to the fixed base 18. Generally, the fixed table 18 has at least one pair of elongated guides 12, each having a flat top surface which slidably supports a bottom surface of the movable top 16 during its displacement. Relative displacement between the top and base 16, 18 is provided by a mechanism 14 actuated by a motor 29, which is shown diagrammatically in FIG. 2. Such mechanism can be, for example, a rack and pinion assembly, wherein a rack mounted to the fixed base 18 meshes with a pinion located in the movable top. The invention is not limited to any particular type of a motion-translating mechanism and can easily utilize a variety of different actuators which, for example, can be a pneumatically or hydraulically operated means.

Examination of the endoscope 50 is performed by controllably rotating a carousel 30, which is fixed to the movable support 28 for synchronous linear motion therewith, with respect to the distal end 52 of the endoscope 50. Particularly, the carousel 30 has a shaft 31 rotatably mounted on the top 16 of the support 28 and actuatable by a motor 25, diagrammatically shown in FIG. 2 to rotate a rotary support 33 (FIG. 4) carrying the array of targets 32 for performing a variety of tests. The shaft 31 displaces the rotary support 33 to enable it to bring each of the targets in a nominal filed of view of the endoscope 50. The term "target" broadly describes any of the various devices used for receiving, generating and reflecting a transmitted beam to evaluate the physical and optical parameters of the endoscope 50.

The array of targets 32 may include a various number of targets depending on a particular group of tests to be conducted. As better shown in FIG. 4, the array includes a diffuse but translucent white target 60, a grid with pinholes target 62, a detector 64 to measure optical power or luminous flux and a single pinhole target 66. This combination of targets mounted on the rotary support 33 allows the inspection system 20 to perform the field of view, geometrical distortion, angle of view, image quality at single and various object distances, percentage light transmission through illumination fibers, relative light transmission through imaging system and illumination intensity tests. Each of the targets can be used for performing either a single or a group of tests, as will be explained hereinbelow.

Figure 5A:
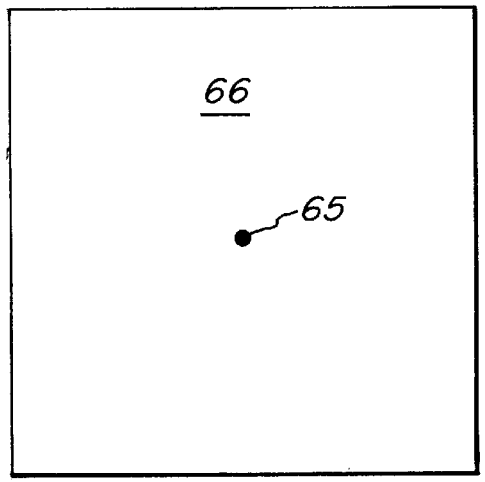
FIGS. 5a and 5b are enlarged schematic views of a pinhole target and a grid target, respectively.
Figure 5B:
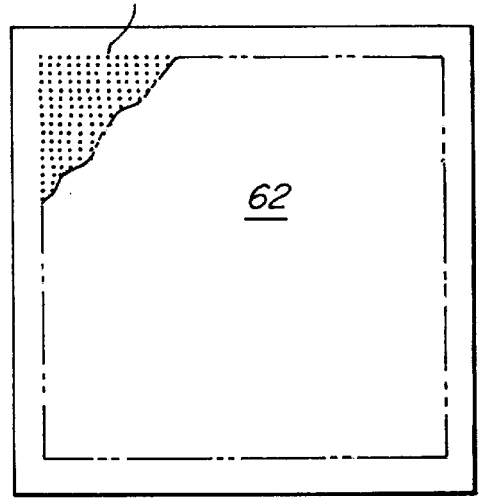

Referring to FIGS. 5a and 5b, the grid target 62 is a plate made of glass and has a series of evenly spaced and uniformly sized pinholes 63 to measure a field of view, distortion, image quality and a depth of field of the endoscope 50, as described in detail in a U.S. application Ser. No. 09/563,867 filed concurrently with this application. The grid target is illuminated by a light source 68 having an EJA lamp rotatable with the carousel about the rotation axis 40 and aligned with the grid target for conducting the above-listed tests. Also, the grid target is capable of performing an angle of view test if a single pinhole is addressable.

Each of the holes is positioned in a center of a respective square. Based on this particular structure a variety of measurements can be easily made by a CPU 44 (FIG. 2) that uses the algorithms as explained in greater detail in the copending U.S. application Ser. No. 09/563,867 filed concurrently with this application.

The single pinhole target 66 may be used for performing angle of view test indicating deviation from the nominal angle of the standard endoscope. It may be made of metal and has a pinhole 65 which has a diameter smaller than a diameter of each of the pinholes 63 of the grid target. This target is illuminated by a fiber optic coupled to another source of light 67 (FIG. 1) which is mounted to the housing.

Figure 6:
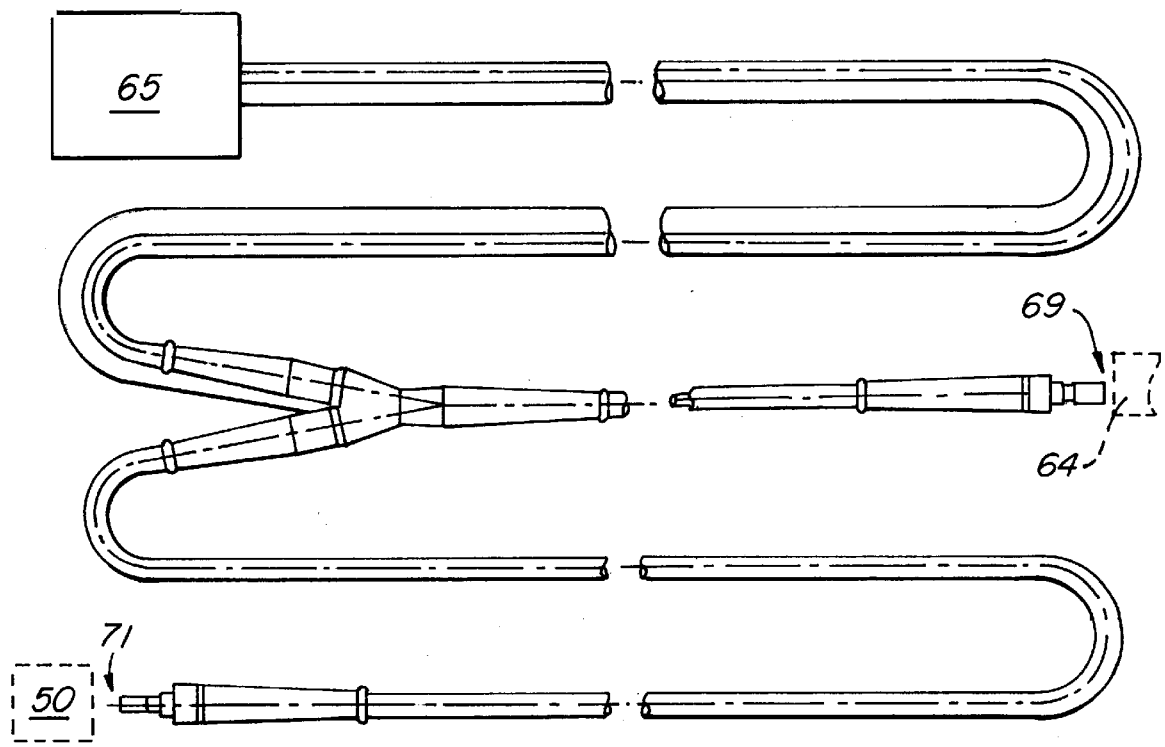
FIG. 6 is a bifurcated cable of the device shown in FIGS. 1 and 2.

According to a feature of this invention, in order to measure the transmission through illumination fibers indicating the percentage of light lost, the system 20 utilizes a bifurcated light guide plugged in a source of light 65 by one of its ends (FIG. 6). The light guide has a bifurcated opposite end including ends 69 and 71. The rational behind using the bifurcated light guide is that the relative illumination through each end is the same because the system and cable are designed to prevent any deviation between the outputs. Thus, if the output of one end is known, then so is the output of the other end. In order to perform this test, the system 20 has a post 73 extending upwardly to a level of the detector 64, which is mounted on the base of the plate of the system housing, and not interfering with displacement of the testing station 24. The detector 64 is rotatable between a first position, wherein it is aligned with the bifurcated end 69 plugged in the post 73 (FIG. 4), and a second position. In the second position, the detector 64 is turned in the nominal angle of the endoscope to be aligned with the distal end of the endoscope 50 connected to the second bifurcated end 71. The percentage light transmission through the illumination fibers can then be calculated:

$$\%T = y\, O_s/O_b$$

where $O_s$ is the output of the endoscope, $O_b$ is the output of the first bifurcated end 69, and y is the ratio of light out of the bifurcated light guide end 71 to the light out of the end attached to the scope.

The white target 60 is used for performing a relative light transmission test through an imaging system including a system of lenses. The white target has approximately the same dimensions as the grid target and is made of opal glass having a piece of diffuse material, such as paper. Similarly to the grid target 62, the white target is slidably supported by a respective frame 75 and is aligned with and illuminated by a respective light source 77 mounted on the carousel 32.

To perform this test, a photo detector, such as a silicone photodiode 45 (FIG. 1), measures the light incident on the white target illuminated by the light source 77. Further, the light transmitted through the endoscope is measured by a camera 58 connected to the proximal end of the endoscope (FIG. 2); the ratio between these two measurements is calculated by the CPU and further compared to the ratio for other endoscopes.

Still another test that can be conducted by means of the white target 60 is the illumination intensity across the field of view of the endoscope which is done by connecting the distal end 52 of the endoscope with the end 71 of the bifurcated light guide. Upon turning on the light source 65, an image of the illumination pattern as seen at the camera 58 is grabbed and seen on a monitor 46 (FIG. 2). The illumination profile test shows a fall off of light from the center to the edge of the field of view of the endoscope.

Thus, as a consequence of the kinematics of the testing station 24 as described above, the endoscope inspection system 20 according to the invention requires a limited space and is capable of testing a variety of endoscopes in an efficient manner.

Figure 7:
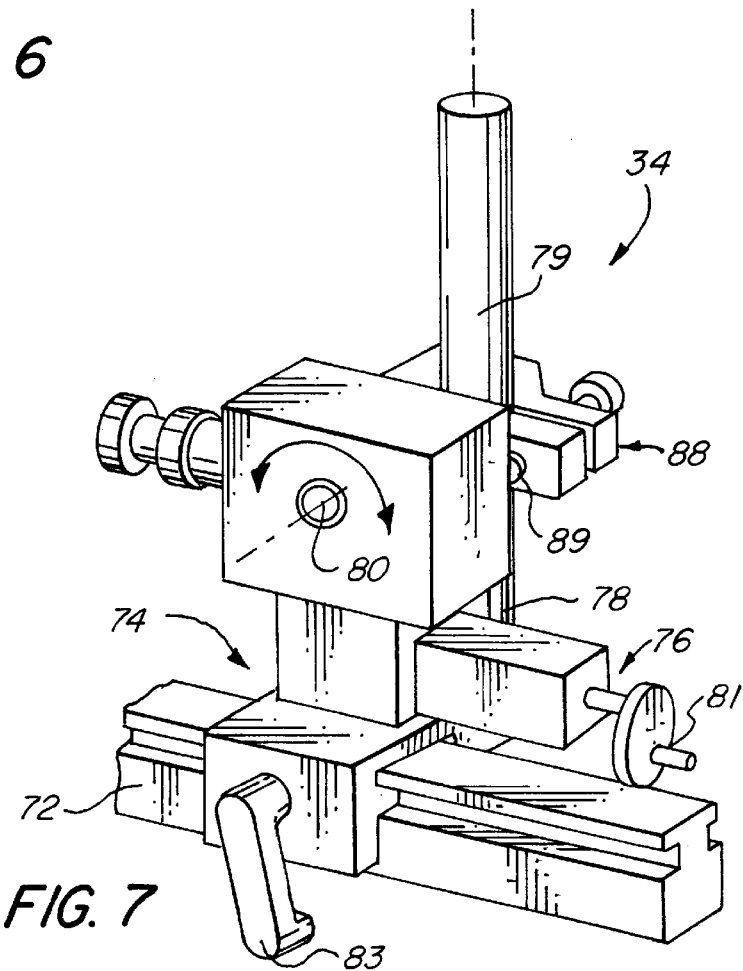
FIG. 7 is an isometric view of an endoscope supporting station of the device shown in FIG. 1.
Figures 8, 9:
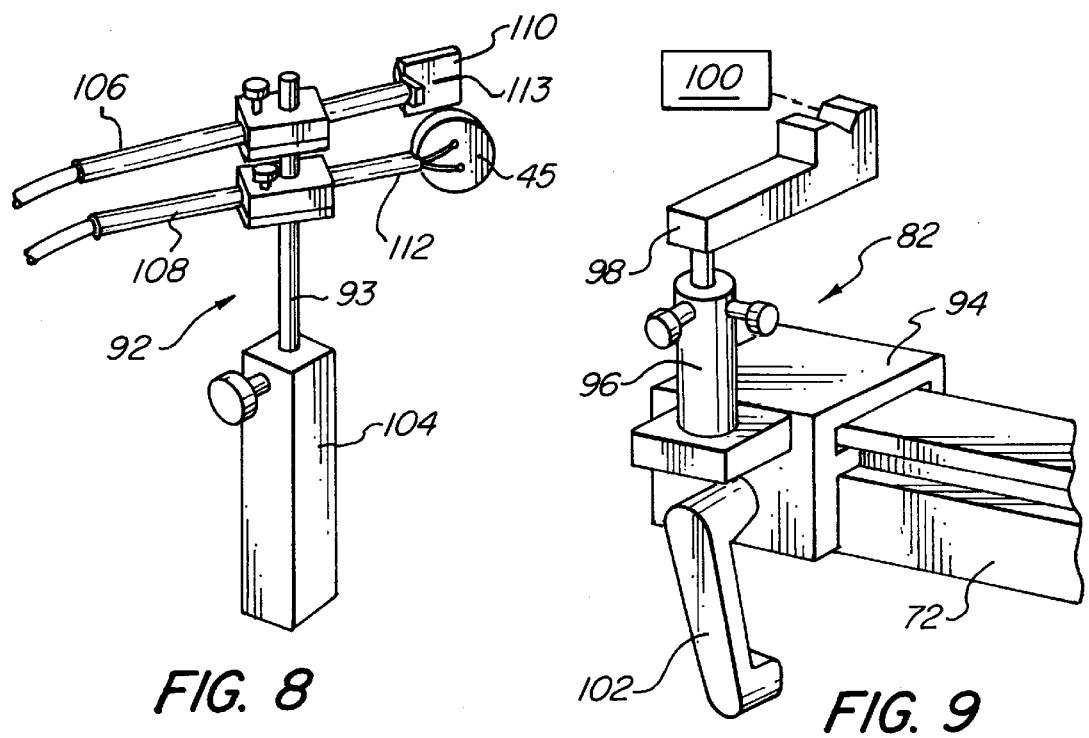
FIG. 8 is an isometric view of an alignment target assembly of the device shown in FIG. 1.
FIG. 9 is an isometric view of a V-block assembly for providing horizontal alignment of an endoscope to be tested.

According to another aspect of the invention, as shown in FIG. 7, the support station 34 allows displacement of the endoscope 50 along x, y and z directions to accommodate differently configured endoscopes and to place them in a predetermined position with respect to the testing station 24.

Particularly, the support station 34 includes a horizontal guide rail 72 receiving a support carriage 74 controllably slidable along the guide rail toward and away from the testing station 24. Mounted on the carriage is a camera support 76 which has a vertically extending post 78 serving as a vertical guide for displacing a mounting bracket 88 receiving the camera 58. If the scope has an offset or angled eyepiece, a mounting bracket 89 can be raised vertically along the length of a support post 78. The mounting bracket 88 is also angularly displaceable about an axis 80 to receive the endoscopes formed with an angled eyepiece. Displacement of the support station can be automatic in response to an input containing information as to a type of the tested endoscope. Alternatively, each of the components of the support station may have a manual actuator, as for example a hand crank 81 allowing a user to displace the support station along the guide rail. Horizontal displacement of the support station may be arrested by using a brake 83 to prevent damage to the array of targets 32 in case of malfunctioning of the system 20.

According to another aspect of the invention, the alignment station 36 acting in cooperation with the support station 34 and an alignment assembly 92 (FIG. 8) allows the endoscope 50 to be properly aligned to obtain accurate measurements. Particularly, the alignment assembly 92 is mounted on the rotary turntable 26 and includes a vertical post 104 rotatable with the turntable and carrying two brackets which receive horizontally extending arms 106 and 108, respectively. The arm 106 carries an alignment target 110, whereas the arm 108 supports the photo detector 45. The arm 106 may be controllably displaced in a respective bracket to occupy a proper position, wherein the alignment target is positioned directly above the center of rotation of the turntable 26. To obtain the proper position, the movable support 28 is displaced to its distant position in a direction of arrow A allowing a shaft 93, which extends from the post 104, to be linearly adjusted in three axes to properly position the arm 106 relative the axis 38 (FIG. 2). This rotation can be performed automatically or manually. Upon completing the positioning of the alignment target, the support station is displaceable to juxtapose the endoscope with the alignment target, whose slit (FIG. 10) is imaged at the monitor upon connecting the bifurcated end 71 of the light guide to the distal end 52 of the endoscope.

A proper vertical position of the support station 34 is achieved by a riser block 90 mounted on the casing 22 and having a roller bearing translator 91 which is actuated to vertically displace the horizontal rail 72 so as to adjust a vertical position of the endoscope 50. A "V" block assembly 82, which is mounted on an opposite end of the horizontal rail 72, has a V-shaped groove that is sized to receive the shaft 56 of the endoscope upon vertical displacement thereof. The block assembly 82 serves to ensure a correct horizontal position of the endoscope and includes a mounting bracket 94 slidable along the rail 72 to a predetermined position. Displacement of the V block assembly along the horizontal rail 72 may be automatically arrested at some distance from the distal end 52 of the scope, typically not exceeding a few centimeters, by actuating a break 102. The bracket 94 supports a telescopically extendable and rotatable post 96 which holds a horizontal arm 98 formed with the V-shaped groove. The post 96 can be displaced automatically by monitoring a position of the V-shaped groove relative to the shaft 56 of the scope by a position sensor 100 to provide a proper positioning of the endoscope in the groove. However, it is also possible to operate displacement of this post manually.

Figures 10A, 10B, 10C:
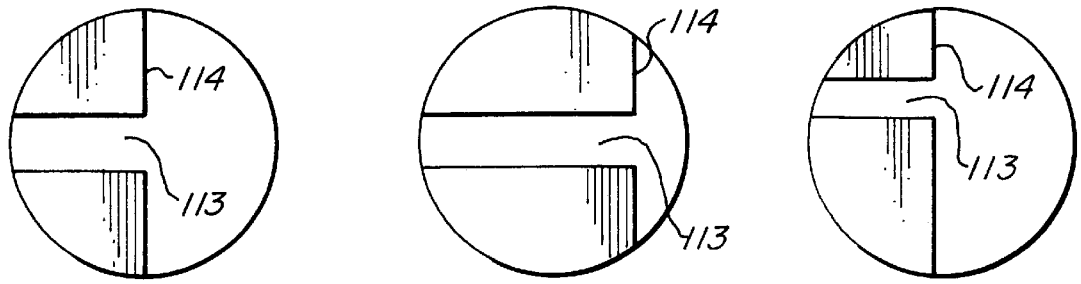
FIGS. 10a–10c illustrate a process of alignment of the endoscope to be tested.

Referring to FIGS. 10a–10c, the alignment target 110 is shown to have a slit 112 formed midway between upper and lower edges of this target. To properly align the scope a vertical edge 114 and the slit 112 have to be centered in the field of view of the endoscope. If an angle of view is noticeably wrong, as shown in FIGS. 10b and 10c, it may be changed by clicking the increase and decrease buttons (not shown) on the monitor 46, which rotate the stage 26.

FIG. 11 is an exemplary display of a graphical user interface provided by the computer 46 (FIG. 2) to set up a test. Besides comparing the tested endoscope with the standard one, parameters of which are stored in the reference data base, there are two different types of additions to this database. First, the user may add a new type of scope and second, the user may want to add another sample of a scope already in the database to increase the statistical sampling. By clicking on a button 122 appeared on the monitor for adding a new scope, the user will be able to introduce a serial number or any other identification of the tested endoscope at 120. A table 116 illustrates test parameters that can be loaded by a user who further may use a table 118 to select tests to be conducted.

FIG. 12 illustrates a table 124 showing comparative results of the scope to be tested with the standard one, which is stored in the database. Illustrative examples showing images of the standard scope and the one to be tested are illustrated on the same screen and are explained in detail in the co-pending U.S. Application Ser. No. 09/563,867 filed concurrently with this application. This display of images and data may be printed by a printer 48.

Figure 13:
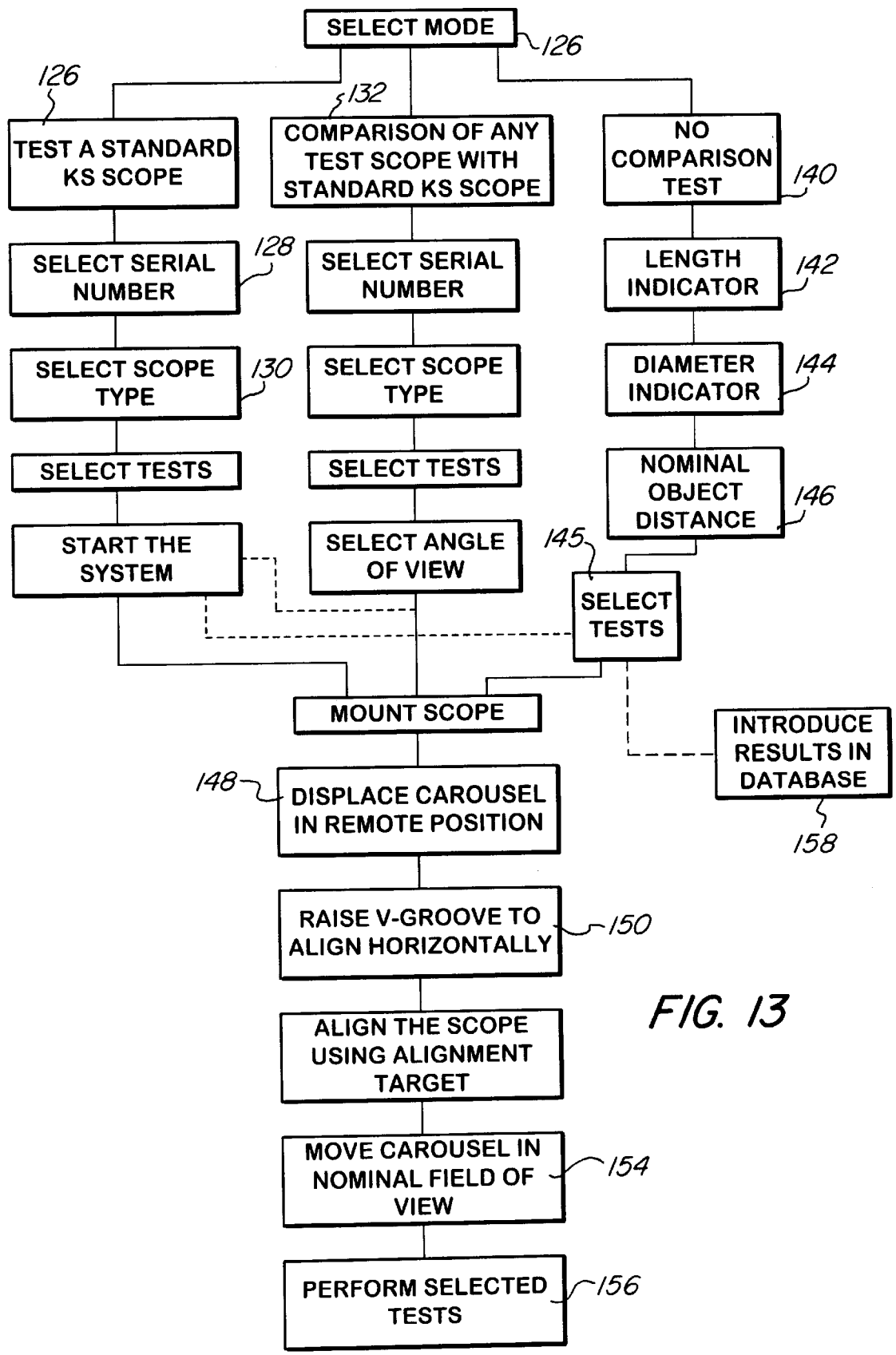
FIG. 13 is a flow chart illustrating conceptually a method of operating the device shown in FIGS. 1 and 2.

FIG. 13 illustrates a flow chart of the system 20 having a plurality of modes in which the system is capable of performing different testing procedures. A user can select a mode at 126 in which a standard Karl Storz endoscope is tested by comparing it with a standard scope of the same type stored in the database. A user has to introduce a stored serial number at 128 and a selected type at 130 before the system can perform a series of tests.

Alternatively, the user can select a mode at 132 in which a tested endoscope for a manufacturer other than Karl Storz can be compared to a standard Karl Storz endoscope stored in the database. Similarly to the first mode, a serial number and scope type to compare to must be input at 134 and 136, respectively. Also, the name of the scope and its serial number must be entered. Since the tested endoscope will be compared with the standard one whose parameters are stored in the database, the nominal angle of view can be changed by the user. This enables, for example, a 25° endoscope to be compared with a 30° Karl Storz endoscope stored in the database.

Finally, the user may select a third mode of operation of the system in which an endoscope can be analyzed without comparison with the standard endoscope at 140. After the test option dialog appears on the monitor, the user can introduce a set of parameters, such as a length, diameter and a nominal distance at 142, 144 and 146, respectively, which are typically based on her experience and knowledge, and if the results are to her satisfaction, they can be stored in the database at 158.

After the mode was selected, the system starts with linearly displacing the carousel in its remote position at 148. Following it, the endoscope is aligned horizontally and vertically at 150 and 152, respectively, and is ready to be tested upon displacing the carousel at the nominal object distance at 154 in response to either the stored parameters of the standard endoscopes or to a set of parameters introduced by the user. After establishing a proper position, the system is ready to perform any of the variety of selected tests at 156 by rotatably displacing the carousel which brings the desirable target in the nominal angle of view. After the procedure has been completed, the results can appear at the monitor and finally printed.

Although the invention has been described with respect to a preferred embodiment thereof, it should be understood that other various modifications and additions thereto may be made without departing from the scope of the invention as defined in the appended claims.

What is claimed is:

1. A endoscope inspection system comprising:
   an endoscope support for mounting an endoscope to be tested;
   a turntable spaced from the endoscope support and rotatable to a nominal angle of the endoscope about a first axis extending substantially vertically to the endoscope; and
   a carousel displaceable with said turntable and carrying a plurality of targets, said carousel being rotatable about a second axis parallel to the first axis to selectively displace each target into a field of view of the endoscope to make an appropriate measurement upon displacing said turntable to the nominal angle.

2. The endoscope inspection system defined in claim 1, further comprising a carousel support mounted rotatably fixed on said turntable and linearly displaceable along a third axis extending perpendicular to the first and second axes away and toward the endoscope.

3. The endoscope inspection system defined in claim 2 wherein said carousel support rotatably supports said carousel displaceable with said carousel support along the third axis with respect to said turntable.

4. The endoscope inspection system defined in claim 3 wherein each of said carousel, carousel support and the turntable has a respective actuator, the actuator being a stepper motor.

5. The endoscope inspection system defined in claim 1 wherein the endoscope support includes a horizontal rail extending parallel to the endoscope and a support carriage and V block assembly mounted on opposite ends of the horizontal rail to controllably slide therealong.

6. The endoscope inspection system defined in claim 5 wherein the V block assembly has a post, a rotatable shaft extending from the post and having a horizontally extending arm with a V-shaped groove guide which is sized to receive a shaft of the endoscope so as to establish a horizontal position thereof upon displacing the block assembly along the rail relative to the endoscope.

7. The endoscope inspection system defined in claim 5 wherein the horizontal rail is mounted on a riser block having a roller bearing translator which is actuated to vertically displace the horizontal rail so as to adjust a vertical position of the endoscope.

8. The endoscope inspection system defined in claim 6 wherein the support carriage is controllably displaceable along the horizontal rail and is stopped at a predetermined distance from the first axis of the turntable upon detecting a predetermined linear position of the support carriage by another positioning sensor.

9. The inspection system defined in claim 6 wherein the support carriage further includes a linear ball bearing or cross roller bearing table slidably mounted on the horizontal rail and a post mounted rotatably on the ball bearing table about a vertical post axis.

10. The inspection system defined in claim 9 wherein a camera mount bracket is mounted on the post and is controllably displaceable along the post, the camera bracket receiving a CCD camera which can be coupled with an eyepiece of the endoscope.

11. The inspection system defined in claim 10 wherein the camera mount bracket is angularly displaceable about a horizontal axis extending perpendicular to the horizontal rail for receiving an endoscope, wherein a shaft extends at an angle to a proximal end of the tested endoscope having an eyepiece.

12. The inspection system defined in claim 9 wherein the linear ball bearing table has a brake for arresting displacement of this table along the horizontal rail.

13. The inspection system defined in claim 1 wherein the turntable has an alignment post displaceable along a vertical axis and having an alignment target mounted on horizontally extending arm, which is displaceable perpendicular to the vertical axis to a predetermined position, wherein the alignment target stops in a plane of the first axis of rotation of the turntable.

14. The inspection system defined in claim 13 wherein the alignment target has a vertical and horizontal slit.

15. The inspection system defined in claim 1 wherein the targets include a first target made of glass and having a plurality of uniform pinholes, each located at a center of a respective square, a second target being a diffuse translucent white target, a third target having a single pinhole with a diameter less than a diameter of the uniform pinholes of the first target and a detector for measuring a luminous flux.

16. The inspection system defined in claim 15 wherein the targets are spaced angularly apart on the carousel, the carousel further supporting a pair of frames slidably receiving the first and second targets, respectively, and at least two sources of light each aligned with a respective one of the frames.

17. The inspection system defined in claim 15 wherein the carousel further supports a photo-detector, the inspection system further comprising a third source of light and a light guide connected to the third source of light.

18. The inspection system defined in claim 17 wherein the light guide is a fiberoptic cable having one end attached to a fourth source of light and an opposite end, the opposite end being bifurcated so as to have one of the bifurcated ends mounted so that the light output can be measured by the photo-detector and the other bifurcated end attached to the endoscope.

19. An inspection system for performing tests selected from the group consisting of field of view, angle of view, distortion, image quality, depth of field, illumination system transmission efficiency, illumination profile, relative transmission of imaging system and centering error of a rigid and a combination thereof for evaluating optical characteristics of endoscope, the system comprising:

a testing station supporting a plurality of targets for measuring an optical performance of the endoscope; and a controller for controllably displacing said testing station linearly toward and away from the endoscope, for controllably rotating said testing station at a nominal angle of view of the endoscope about a first axis, and for controllably rotating said targets about a second axis parallel to the first axis to selectively displace each of the targets into the field of view of the endoscope.

20. The inspection system defined in claim 19 wherein the controller includes a database storing a plurality of standardized parameters and a comparator evaluating the results of the tests on the endoscope to be tested with the standardized parameters.

* * * * *